United States Patent [19]

Kurakake

[11] Patent Number: 5,198,680

[45] Date of Patent: Mar. 30, 1993

[54] HIGH PRECISION SINGLE FOCUS COLLIMATOR AND METHOD FOR MANUFACTURING HIGH PRECISION SINGLE FOCUS COLLIMATOR

[75] Inventor: Tadakazu Kurakake, Tokyo, Japan

[73] Assignee: Kabushiki Kaisha Toshiba, Tokyo, Japan

[21] Appl. No.: 858,709

[22] Filed: Mar. 27, 1992

[30] Foreign Application Priority Data

Mar. 27, 1991 [JP] Japan .................................. 3-63522

[51] Int. Cl.$^5$ .............................................. G21K 1/02
[52] U.S. Cl. .................................. 250/505.1; 378/147; 378/149; 164/98
[58] Field of Search ........... 250/505.1, 363.01, 363.04; 378/147, 149; 164/98

[56] References Cited

U.S. PATENT DOCUMENTS

| | | | |
|---|---|---|---|
| 2,806,958 | 9/1957 | Zunick | 250/505.1 |
| 4,250,392 | 2/1981 | Leask et al. | 250/505.1 |
| 4,563,583 | 7/1986 | Hattori | 250/505.1 |
| 4,958,081 | 9/1990 | Malmin et al. | 250/505.1 |
| 5,099,134 | 3/1992 | Hase et al. | 250/505.1 |

FOREIGN PATENT DOCUMENTS 0212416 3/1987 European Pat. Off. .
1493267 11/1977 United Kingdom .

OTHER PUBLICATIONS

Nuclear Fields Precision Micro-cast Collimators, Nuclear Fields Pty Ltd., (sales brochure) "Giving you the Complete Picture", 9 pages.
Nuclear Fields: Micro-cast Collimators and Associated Nuclear Medical Products, Nuclear Fields Inc., (sales brochure), 8 pages.
Patent Abstracts of Japan, vol. 9, No. 314, (P-412) [2037], Dec. 10, 1985, & JP-A-60-144683, Jul. 31, 1985, T. Shibahara, "Manufacture of Collimator for Radiation".
Patent Abstracts of Japan, vol. 9, No. 133, (P-362) [1856], Jun. 8, 1985, & JP-A-60-17380, Jan. 29, 1985, Y. Gotou, et al., "Faulted Collimator and Its Production".
Patent Abstracts of Japan, vol. 7, No. 125, (P-200) [1270], May 31, 1983, & JP-A-58-42986, Mar. 12, 1983, Y. Gotou, et al., "Manufacture of Honeycomb Structure with Unidirectional Focus".

Primary Examiner—Jack I. Berman
Assistant Examiner—Kiet T. Nguyen
Attorney, Agent, or Firm—Oblon, Spivak, McClelland, Maier & Neustadt

[57] ABSTRACT

A method for manufacturing a single focus collimator in a high precision without increasing a cost for manufacturing. In this method, grooves are on a bulk block member first, and a metallic material having sufficient γ ray shielding property such as lead is casted into the grooves formed on the bulk block member, and then the bulk block member with the metallic material casted into the grooves is immersed into a solvent capable of dissolving the bulk block member but not the metallic material, such that a collimator body formed by the metallic material in a shape of the grooves is obtained as the bulk block member is dissolved by the solvent. The sensitivity of the single focus collimator can be made substantially uniform over the entire effective view field by forming the grooves with such intervals that holes formed on the collimator body have larger size toward a center of the collimator body.

14 Claims, 3 Drawing Sheets

FIG.1A
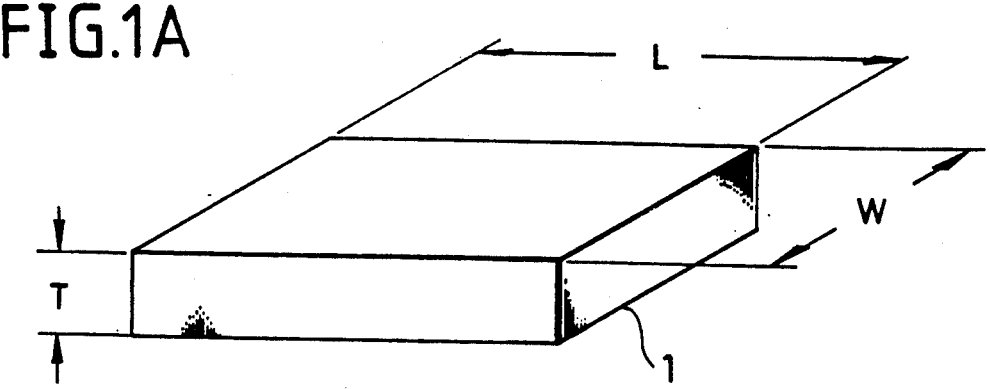
FIG.1B
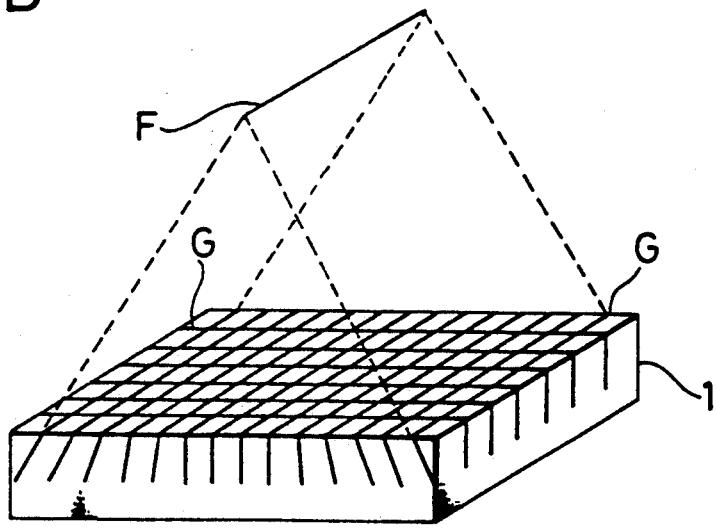
FIG.1C
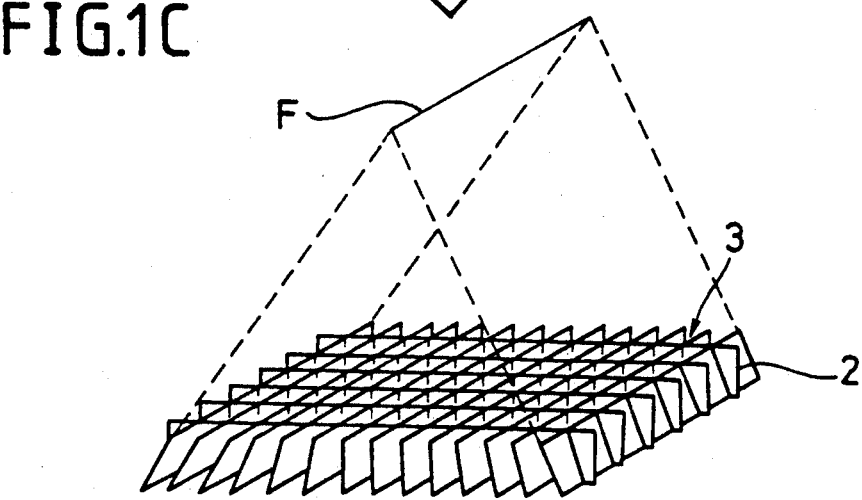

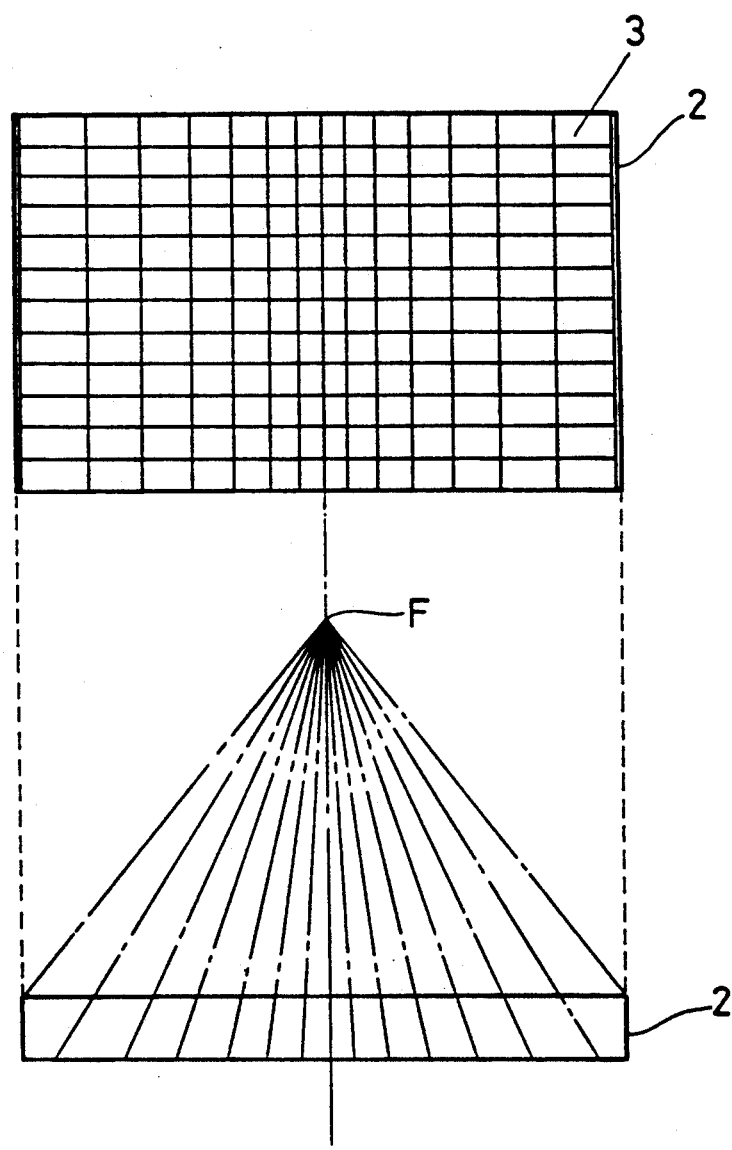

HIGH PRECISION SINGLE FOCUS COLLIMATOR AND METHOD FOR MANUFACTURING HIGH PRECISION SINGLE FOCUS COLLIMATOR

BACKGROUND OF THE INVENTION

1. Field of the Invention

The present invention relates to a collimator to be used in a nuclear medical apparatus such as a SPECT (Single Photon Emission Computed Tomography) apparatus, and a method for manufacturing such a collimator.

2. Description of the Background Art

In a nuclear medical apparatus such as a SPECT apparatus, γ rays emitted from radioactive materials deposited inside a body to be examined are detected, and an image of a distribution of the radioactive materials inside the body is obtained on a basis of the detected γ ray signals, where the obtained image is utilized in the diagnosis of a cancer and a tumor. In such a nuclear medical apparatus, a collimator is attached on a detector device in order to selectively collect the γ rays from the radioactive materials inside the body at the detector device. The γ rays selectively collected at the detector device by using the collimator are then converted into light signals and then into electric signals by using a scintillator, and the obtained electric signals corresponding to the detected γ rays are utilized as the image data in the image reconstruction process.

For such a collimator to be used in a nuclear medical apparatus, there are several types including a parallel hole collimator in which all the holes arranged in an array are parallel to each other, and a single focus (fan beam) collimator in which each hole in an array is provided with a prescribed inclination angle such that the collimator as a whole has a focal line in order to improve the sensitivity and the resolution of the collimator.

In the SPECT apparatus for the head portion diagnosis, three such collimators are used in an arrangement in which each collimator is located on each side of an equilateral triangle formed by detectors arranged around the head portion of a patient.

Among the various types of such a collimator, the parallel hole collimator has conventionally been manufactured by the following methods relatively easily.

(1) A method of folded foil construction in which corrugated thin plates made of lead are piled up to form a collimator body.

(2) A method in which pipe shaped members made of lead are glued together to form a collimator body.

On the other hand, the single focus collimator has been more difficult to manufacture conventionally, because each hole in the array must be manufactured to be oriented toward a single focal line, and the following manufacturing methods have been employed for the single focus collimator conventionally.

(1) A method using pins in which approximately thirty to fifty thousand pins each in a shape of a hole of a collimator to be manufactured are mounted between two templates with pre-manufactured pin positions in an array such that all the pins are oriented toward a predetermined single focal line, and then the lead is casted between the templates with the pins mounted, such that a desired single focus collimator body with all the holes arranged in an array oriented toward the predetermined single focal line can be obtained by pulling out all the pins after the lead casting.

(2) A method using tungsten plates as disclosed in U.S. patent application Ser. No. 07/538,763, in which one type of tungsten plates are provided with fan shape patterned grooves oriented toward a common focal point while the other type of tungsten plates are provided with parallel grooves, such that these two types of tungsten plates can be assembled into a lattice shape by perpendicularly engaging the fan shaped grooves on one type of the tungsten plates with the parallel grooves of the other type of the tungsten plates, so as to form a desired single focus collimator body with all the holes arranged in an array oriented toward the predetermined single focal line.

However, such conventional methods of manufacturing a single focus collimator have been associated with the following problems.

First of all, as for the method using pins, the following three problems exited.

(1) Each of the normally thirty to fifty thousand pins used in manufacturing one single focus collimator must be applied with a tapering process in order to facilitate an easy pulling out operation after the lead casting, so that a number of processes for preparing the pins can be enormously large as well as ineconomical.

(2) Each of the normally thirty to fifty thousand pins used in manufacturing one single focus collimator must be mounted between the templates one by one and them pulled out after the lead casting one by one, all manually, so that the amount of work required for the worker can be enormously large as well as ineconomical.

(3) The precision of the manufactured single focus collimator is often deteriorated by the bending of the very thin templates due to the weights of the pins, and by the inaccuracy of the pin orientation due to the looseness of the fitting of the pins at the pin positions on the templates.

On the other hand, as for the method using tungsten plates, the following two problems exited.

(1) Each plate to form a collimator body is required to have a thickness of approximately 0.2 mm, so that the material for each plate must have a sufficient rigidity to be able to maintain its shape in such a thin thickness, along with a sufficient γ ray shielding property. For this reason, the tungsten is an only presently available metallic material for each plate. However, the tungsten is a rare metal which is very expensive, so that the cost for manufacturing the collimator inevitably becomes very high. In this regard, if the lead which has the sufficient γ ray shielding property and is relatively inexpensive is to be used for the material for each plate, the plate manufactured in a thickness of approximately 0.2 mm would not be able to maintain its shape in the assembling operation because the lead does not have the sufficient rigidity.

(2) In order to cut the tungsten plates to form the grooves thereon, it becomes necessary to utilize the wire cut electric spark manufacturing process because of the high rigidity of the tungsten. However, such a wire cut electric spark manufacturing process is very time consuming, and therefore the cost for manufacturing the collimator inevitably becomes high.

Moreover, the conventional single focus collimator is also associated with the problem that the sensitivity becomes higher in a central region compared with peripheral regions, such that the appropriate correction of the detector output has been necessary.

SUMMARY OF THE INVENTION

It is therefore an object of the present invention to provide a method for manufacturing a single focus collimator in a high precision, without increasing a cost for manufacturing.

It is another object of the present invention to provide a single focus collimator which can be manufactured in a high precision inexpensively.

Furthermore, it is another object of the present invention to provide a single focus collimator with a uniform sensitivity, which can be manufactured in a high precision inexpensively.

According to one aspect of the present invention there is provided a method for manufacturing a single focus collimator, comprising the steps of: forming grooves on a surface of a bulk block member; casting a metallic material having a sufficient $\gamma$ ray shielding property into said grooves formed on said bulk block member; and immersing said bulk block member with said metallic material casted into said grooves into a solvent capable of dissolving said bulk block member but not said metallic material, such that a collimator body formed by said metallic material in a shape of said grooves is obtained as said bulk block member is dissolved by said solvent.

According to another aspect of the present invention there is provided a single focus collimator, comprising: first septa members arranged in a fan shape pattern in which all the first septa members are oriented toward a common focal line; and second septa members arranged to be parallel to each other, which are perpendicularly crossing with the first septa members in a lattice shape such that holes are defined between each adjacent first septa members and each adjacent second septa members; wherein the first and second septa members are arranged with such intervals that the holes have larger size toward a center of said collimator body.

Other features and advantages of the present invention will become apparent from the following description taken in conjunction with the accompanying drawings.

BRIEF DESCRIPTION OF THE DRAWINGS

FIGS. 1A, 1B, and 1C are sequential illustrations of one embodiment of a method for manufacturing a single focus collimator according to the present invention.

FIG. 2 is an illustration of top plan view and side view of one embodiment of a single focus collimator with improved sensitivity according to the present invention.

DETAILED DESCRIPTION OF THE PREFERRED EMBODIMENTS

Figure 3:
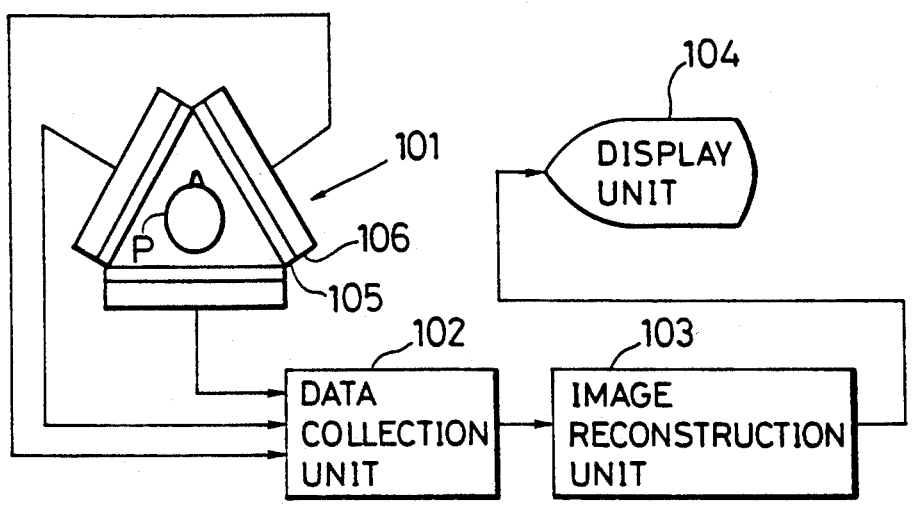
FIG. 3 is a schematic diagram of a SPECT apparatus in which the single focus collimator according to the present invention is to be used.

Referring now to FIG. 1, one embodiment of a method for manufacturing a single focus collimator according to the present invention will be described.

First, as shown in FIG. 1A, a bulk block member 1 made of an aluminum plate is prepared in thickness T=60 mm, length L=400 mm, and width W=200 mm, for example.

Then, as shown in FIG. 1B, fine grooves G of approximately 0.2 mm in width and 40 mm in depth each are formed on an upper surface of the bulk block member 1. The width of each groove G is selected from the preferable range of 0.1 to 1 mm. Here, the grooves G in the length L direction are cut perpendicularly and arranged to be parallel with each other, while the grooves G in the width W direction are cut in a fan shape pattern such that they are oriented toward a common focal line F.

This cutting of the grooves G can be achieved by using a wire cut electric spark manufacturing process under the numerical control, although the use of the wire cut electric spark manufacturing process can be time consuming and therefore expensive. More preferably, the cutting of the grooves G can be achieved by using a disk cutter device under the numerical control. Here, the use of the presently available disk cutter device is possible because the grooves G are to be formed on the aluminum bulk block member 1, and preferable because of the cheaper cost required for such a manufacturing by the disk cutter device compared with the use of the wire cut electric spark manufacturing process. Note also that this disk cutter device cannot be used in the conventional method using the tungsten plates since the presently available disk cutter device is unable to cut the tungsten plates because of the very high rigidity of the tungsten.

Next, the lead is casted into the grooves G formed on the bulk block member 1. In this step, in order to secure the ample casting of the lead into the fine grooves G, the melt lead may be pressurized, or the chemical such as antimony may be added into the lead.

After this lead casting, the whole bulk block member 1 with the lead casted into the grooves G are immersed into a solvent made of strong acid such as hydrochloric acid, sulfuric acid, or nitric acid, or else strong alkali such as sodium hydroxide which can dissolve the aluminum bulk block member 1 but not the lead cast.

As a result, as shown in FIG. 1C, a desired single focus collimator body 2 with all the holes 3 arranged in an array oriented toward the predetermined single focal line F can be obtained from the lead cast which is not dissolvable by the solvent. Note here that the relatively low rigidity of the lead does not cause any trouble in this embodiment because the entire collimator body 2 is formed integrally in a lattice shape and therefore no assembling process is necessary.

In the practical collimator, the collimator body 2 so manufactured will be mounted on a metallic frame for supporting the collimator body 2, and then covered by a cover member for protecting the collimator body 2.

In this procedure of this embodiment, it becomes possible to achieve the precision of approximately 0.05 mm required for the single focus collimator. Here, the wire cut electric spark manufacturing process is capable of achieving the precision as high as 0.001 mm, but the precision of the collimator body 2 after the casting becomes approximately 0.05 mm after the casting.

It is to be noted that, instead of using the bulk block member 1 made of aluminum and the solvent made of hydrochloric acid or sodium hydroxide, the bulk block member 1 made of sodium chloride may be used. In such a case, the solvent made of water can be used for dissolving the bulk block member 1, so that the cost for manufacturing can be reduced considerably.

Now, just as in the conventional collimator, when all the holes 3 are made in the same size, the sensitivity of the collimator body 2 becomes higher in a central region compared with peripheral regions.

In order to make the sensitivity of the collimator body 2 substantially uniform over the entire view field, the size of the holes 3 should be made narrower toward the center, as shown in FIG. 2. For example, the width of the hole 3 at the center can be set to be 1 mm, while the width of the hole 3 at the periphery can be set to be 1.4 mm.

In addition, the further treatment for making the sensitivity of the collimator body 2 uniform such as the shaping of the surface of the collimator body 2 may additionally be applied.

It is to be noted here that in the conventional method using pins, manufacturing of such a configuration in which the size of the holes 3 is made to be narrower toward the center would be extremely time consuming and costly because a large number of pins of different sizes must be prepared in advance.

Such a single focus collimator according to the present invention is intended to be useful primarily in the SPECT apparatus.

More specifically, the SPECT apparatus in which the single focus collimator according to the present invention is to be used has a schematic configuration as shown in FIG. 3. This SPECT apparatus of FIG. 3 comprises: a frame 101 placed around the head portion of the patient P; three γ ray detector devices 106 (each including a scintillator and a photoelectric converter) for detecting the γ rays emitted from radioactive materials deposited inside the patient P and outputting the electric signals corresponding to the detected γ rays, which are mounted on the frame 101 and arranged in a form of an equilateral triangle with the head portion of the patient P located inside; three single focus collimators 105 detachably mounted on the front sides of these γ ray detector devices 106 facing toward the patient P; a data collection unit 102 for collecting the γ rays signals outputted from the γ ray detector devices 106; an image reconstruction unit 103 for carrying out the image reconstruction process by using the detected γ ray signals collected by the data collection unit 102 as the projection image data in order to obtain an image of a distribution of the radioactive materials inside the patient P; and a display unit 104 for displaying the obtained image of a distribution of the radioactive materials inside the patient P for the sake of the diagnosis of a cancer and a tumor.

Figure 4:
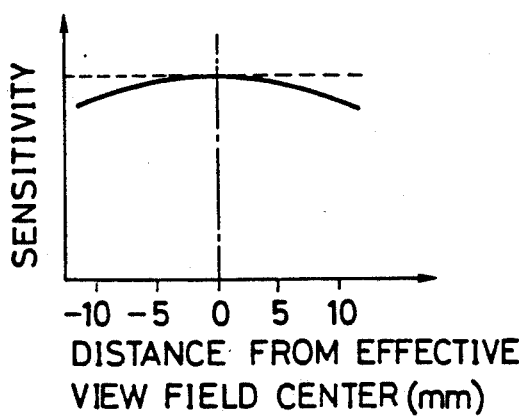
FIG. 4 is a graph showing the sensitivity of the $\gamma$ ray detection in the SPECT apparatus of FIG. 3 when a single focus collimator with a constant hole size is used.

In this SPECT apparatus of FIG. 3, when the single focus collimators 105 of the type in which all the holes are made in the same size throughout the effective view field of the γ ray detector devices 106 are used, the sensitivity of the γ ray detection is not uniform over the entire effective view field and becomes higher in a central region compared with peripheral regions, as shown in FIG. 4.

Figure 5:
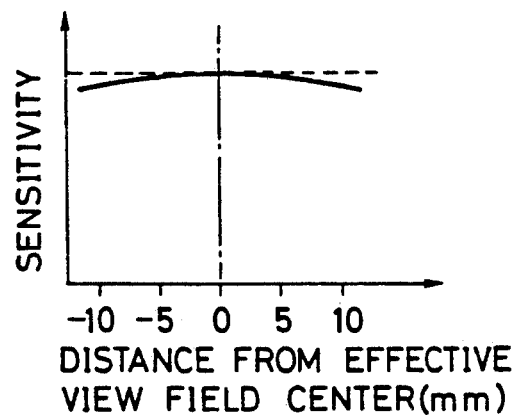
FIG. 5 is a graph showing the sensitivity of the $\gamma$ ray detection in the SPECT apparatus of FIG. 3 when the single focus collimator of FIG. 2 is used.

On the other hand, when the single focus collimators of the type shown in FIG. 2 described above in which the size of the holes are made narrower toward the center are used, the sensitivity of the γ ray detection can be made substantially uniform over the entire effective view field as shown in FIG. 5, so that the complicated correction of the detector output becomes unnecessary in the SPECT apparatus.

As described, according to the present invention, it becomes possible to manufacture a single focus collimator in a high precision, without increasing a cost for manufacturing, because the tedious preparatory and manual works as well as the source for the deterioration of the precision involved in the conventional method using pins are totally absent in the method of the present invention, while at the same time the use of the very expensive tungsten and the very time consuming wire cut electric spark manufacturing process involved in the conventional method using tungsten plates can be avoided in the method of the present invention. Consequently, by using the method of the present invention, it becomes possible to provide a single focus collimator which can be manufactured in a high precision inexpensively.

Furthermore, according to the present invention, it also becomes readily possible to provide a single focus collimator with a uniform sensitivity which can be manufactured in a high precision inexpensively.

It is to be noted that, contrary to the configuration of FIG. 2, the size of the holes 3 may be made wider toward the center, to make the collimator body 2 with a sharply concentrated high sensitivity region around the center, which may be useful in a case of examining a small size target.

It is also to be noted that a so called septa thickness determined by the width of the grooves G may be varied in different sections of the collimator body 2 in order to realize the different γ ray shielding properties at different sections of the collimator.

Besides these, many modifications and variations of the above embodiments may be made without departing from the novel and advantageous features of the present invention. Accordingly, all such modifications and variations are intended to be included within the scope of the appended claims.

What is claimed is:

1. A method for manufacturing a single focus collimator, comprising the steps of:
    forming grooves on a surface of a bulk block member;
    casting a metallic material having a sufficient γ ray shielding property into said grooves formed on said bulk block member; and
    immersing said bulk block member with said metallic material casted into said grooves into a solvent capable of dissolving said bulk block member but not said metallic material, such that a collimator body formed by said metallic material in a shape of said grooves is obtained as said bulk block member is dissolved by said solvent.

2. The method of claim 1, wherein said metallic material is made of lead.

3. The method of claim 1, wherein at the forming step, said grooves are formed by using a disk cutter device.

4. The method of claim 1, wherein at the forming step, said grooves are formed by using a wire cut electric spark manufacturing process.

5. The method of claim 1, wherein said bulk block member is made of aluminum.

6. The method of claim 5, wherein said solvent is made of strong acid.

7. The method of claim 5, wherein said solvent is made of strong alkali.

8. The method of claim 1, wherein said bulk block member is made of sodium chloride.

9. The method of claim 8, wherein said solvent is made of water.

10. The method of claim 1, wherein each of said grooves is formed with a width in a range of 0.1 to 1 mm.

11. The method of claim 1, wherein said grooves are formed with such intervals that holes formed on said collimator body have larger size toward a center of said collimator body.

12. The method of claim 1, wherein said grooves are formed with such intervals that holes formed on said collimator body have smaller size toward a center of said collimator body.

13. The method of claim 1, wherein said grooves are formed with such widths that septa thicknesses of different sections of said collimator body are different.

14. A single focus collimator manufactured by a process comprising the steps of:
    forming grooves on a surface of a bulk block member;
    casting a metallic material having a sufficient $\gamma$ ray shielding property into said grooves formed on said bulk block member; and
    immersing said bulk block member with said metallic material casted into said grooves into a solvent capable of dissolving said bulk block member but not said metallic material, such that a collimator body formed by said metallic material in a shape of said grooves is obtained, as said bulk block member is dissolved by said solvent.

* * * * *